United States Patent [19] [11] Patent Number: 5,922,006
Sugerman [45] Date of Patent: Jul. 13, 1999

[54] NASAL APPLIANCE

[76] Inventor: Joseph H. Sugerman, 350 S. Glenroy Ave., Los Angeles, Calif. 90049

[21] Appl. No.: 08/901,931

[22] Filed: Jul. 29, 1997

Related U.S. Application Data

[60] Provisional application No. 60/023,838, Aug. 12, 1996.
[51] Int. Cl.[6] ........................................................ A61F 5/08
[52] U.S. Cl. ................................ 606/204.45; 606/204.15
[58] Field of Search ........................ 606/204.45, 204.15, 606/198, 199; D24/135; 506/201

[56] References Cited

U.S. PATENT DOCUMENTS

| D. 325,439 | 4/1992 | Apple et al. |
| 1,034,123 | 7/1912 | Knowlson ............................ 606/204.45 |
| 1,077,574 | 11/1913 | Woodward .......................... 606/204.45 |
| 2,515,756 | 7/1950 | Bove . |
| 5,476,091 | 12/1995 | Johnson ................................ 128/200.4 |
| 5,479,944 | 1/1996 | Petruson . |
| 5,522,837 | 6/1996 | Latina .................................... 606/201 |

FOREIGN PATENT DOCUMENTS

WO 96/01093  1/1996  WIPO .

OTHER PUBLICATIONS

Damark Catalog p. 52: Snor Stop 2000 Direct Marketing Enterprises Catalog p. 46: Breathe Relief.

Primary Examiner—Michael Buiz
Assistant Examiner—Vy Q. Bui
Attorney, Agent, or Firm—Henry M. Bissell

[57] ABSTRACT

A device for enabling a person to breathe more easily while alleviating snoring problems. The device is a generally W-shaped frame providing a pair of suitably sized spacing tips for insertion into the user's nostrils. These tips serve to open and shape the nasal passages so that breathing is facilitated.

27 Claims, 1 Drawing Sheet

NASAL APPLIANCE

CROSS-REFERENCE TO RELATED APPLICATION

This application claims the benefit of U.S. Provisional Application No.: 60/023,838, filed Aug. 12, 1996.

BACKGROUND OF THE INVENTION

1. Field of the Invention

This invention relates to devices and methods used to improve breathing through a person's nasal passageways and, more particularly, to devices and methods used to alleviate snoring and ease breathing.

2. Description of the Related Art

For a number of years, prior art devices have sought to alleviate snoring and ease breathing through a variety of methods. The prior art Breathe Eeze™ internal nostril dilators consist of a pair of barrel-shaped corrugated springs. The barrels are to be inserted, one in each nostril, to stretch the nostril.

The prior art Breathe Rite® nose strips consist of a spring member strip with an adhesive backing. The device enlarges the nasal passageways through the affixing of the flexible adhesive strip, low across the bridge of the nose.

The prior art Nozovent™ device consists of a latex spring member having a paddle on each end. The device is flexed into a U-shape and inserted to permit the paddles to exert spring force against the interior of each nostril and stretch them open.

The prior art also includes a variety of devices, e.g. Snore Stop 2000™, Breathe EZ™, that stimulate the nerves of the septum to open nasal passages by way of a flexible U-shaped clip that is inserted to pinch the septum.

While the prior art devices are functional, each has attendant disadvantages. The barrel-shaped dilators can be difficult to insert and have remain inserted. The pressure of the metal spring on the user's skin may cause irritation at the point of contact. Additionally, continued use of the dilators may stretch the nostrils, presenting undesirable cosmetic effects.

With regard to the adhesive nose strips, the adhesive can irritate and damage the user's skin where applied. Additionally, the device must be applied to clean, dry skin in order to be properly affixed. The effectiveness of the adhesive of the device is impaired by the presence of dirt, water, and oil on the skin of the user. Finally, the prior art device is not reusable but must be discarded after use, thus increasing the cost of repeated use.

The use of the paddle-ended spring member has the potential of permanently stretching the nostrils at the base, as well as the application of uncomfortable continuous pressure. This device also pulls the nostrils open at the base, when the cause of the increased breathing resistance is found higher up inside the nasal passageway.

The U-shaped clip devices attempt to stimulate the nerves of the septum, in efforts to open swollen passages, but do nothing to reshape the external passageway to reduce breathing resistance. The continuous pressure exerted by these devices may cause irritation and discomfort.

Correcting defects in the nasal valve and enlarging the cross-sectional area of the nasal passageway through the reshaping of the nasal fossae (with a graft at the apex) is a recognized surgical procedure. However, the discomfort and expense associated with such a procedure seriously limits its appeal as a potential treatment.

SUMMARY OF THE INVENTION

In brief, particular arrangements in accordance with the present invention include a specially shaped frame having a pair of spacing tips adapted for insertion into the nasal fossae to expand the breathing passages when the device is in use. Each spacing tip covers the free end of a corresponding strut provided at an associated frame end such that the tipped struts can be inserted into, and maintain their position within, the nostrils of the user.

Such arrangements of the present invention address and remedy the deficiencies inherent in the prior art. The present invention does not stretch the nostrils, and does not exert pressure on the septum. The present invention is not primarily dependent upon adhesives which may irritate and/or damage the user's skin. Additionally, the present invention does not require clean and/or dry skin in order to be fully functional, as its use is not affected by the presence of dirt, water, or oil on the user's skin. Finally, the present invention is reusable. These features provide the user with a level of convenience and cost effectiveness far beyond that provided by known prior art devices.

The present invention provides the full benefit of the common surgical methods used to treat conditions such as snoring or difficulty in breathing. Yet these benefits are achieved without the discomfort and great expense which accompany such surgical procedures.

The present invention improves the flow of air through the nose through a stenting, i.e. preventing collapse, of the cartilages of the nose on inspiration. The mechanism of action may be more easily understood with the following conceptual model. Imagine the anatomy of the nose as a simple tent open at both ends. However, instead of tent poles holding up the tent, a wall-like partition exists between the two sides. This wall is the nasal septum, dividing the two nostrils, and the sides of the tent represent the cartilages of the nostrils.

In a normal nose, air flows smoothly through the two sides of the tent as breathing occurs. As inhalation effort increases, so does the likelihood of collapse of the sides of the nose due to the venturi effect. Referring to our tent model, the apex of the tent, i.e. the area where the sides come together with the wall at the top of the tent, exerts the most critical influence on air flow. In the nose, the portion of the apex near the front of the nose forms the upper part of what is referred to as the nasal valve. The present invention acts at this area, serving to prevent collapse of the nostrils when air is inspired.

Even in a normal nose, collapse of the nostrils will occur as air flow speed is increased. In persons with distorted nasal anatomy, the effects are far worse. If a person has a deviated septum, which may be thought of as a "warped" wall of the tent, increased effort is required to move the same volume of air through the nasal valve. This increased effort may manifest itself as snoring.

Finally, if the sides of the tent are narrowed at the top, as is commonly seen after cosmetic surgery to narrow the tip of the nose, the some effects are noted; i.e. increased effort is required to pass a given volume of air through a narrowed passageway.

The present invention serves to prevent collapse of the sides of the nose from the venturi effect as described above. The present invention maintains patency of the apex of the nasal valve during inspiration through the stenting of the cartilages of the nose by the placement of spacing tips at the apex of the nasal valve.

One particular arrangement in accordance with the present invention comprises a device having a generally W-shaped frame, also can be described as a frame formed with a pair of Us joined by a transverse bridge, terminating in a pair of spacing tips. The device is dimensioned and shaped so that the spacing tips may be inserted into the outer ends of one's nasal passages (the nasal fossae). The frame is preferably fabricated of a spring material exhibiting a degree of malleability, such as copper or stainless steel or a suitable plastic, rubber, silicone or the like, so that the device can be easily fitted to an individual user. The spacing tips may be enlarged attachments placed over the ends of a pair of intra-nasal struts which form the ends of the frame that is bent and shaped to bridge the nostrils. Preferably, each spacing tip is made of a hypo-allergenic, non-irritating, cushioning material such as surgical-grade silicone. If the frame is fabricated of a suitable material, the entire unit, including the spacing tips, may be integrally formed as one.

DESCRIPTION OF THE DRAWINGS

A better understanding of the present invention may be realized from a consideration of the following detailed description, taken in conjunction with the accompanying drawings, in which.

DETAILED DESCRIPTION OF THE PREFERRED EMBODIMENTS

Figure 1:
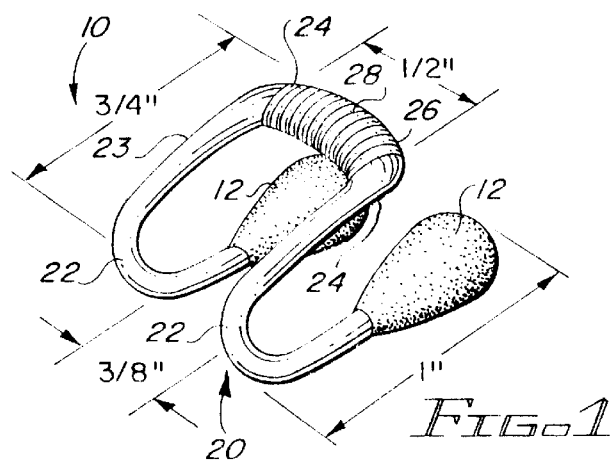
FIG. 1 is a perspective view of one arrangement of the present invention and identifies some of the approximate dimensions of the device.
Figure 5:
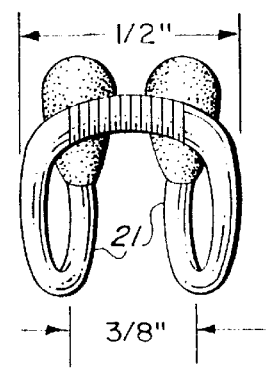
FIG. 5 is a top view of the arrangement of FIG. 1, again identifying some of the approximate dimensions of the device.
Figure 6:
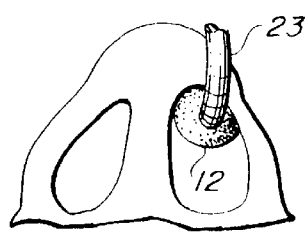
FIG. 6 is a partial view of one part of the device in place, showing the increased cross-sectional area that is achieved through the use of the device (left nasal passageway) in comparison with the shape of the nasal passageway without the device (right nasal passageway)

The present invention will be described in greater detail by reference to the drawing figures. FIG. 1 shows a device 10 embodying the present invention. The device 10 eases breathing and enlarges the nasal passageways by properly positioning each of a pair of spacing tips 12, shown in FIG. 1, within the nasal fossae. Each spacing tip 12 measures approximately ⅜" in diameter and approximately ½" in length. In order to fit a wide variety of noses, several sizes of the present invention may be offered. The spacing tips 12 may vary from 1/16" to ⅜" in diameter and may vary from 1/16" to ½" in length. For comfort and cleanliness, each spacing tip 12 is made of a hypo-allergenic, non-irritating, cushioning material, such as surgical grade silicone. If desired, the spacing tips 12 may be formed of latex rubber, polyurethane or ordinary plastic. The spacing tips 12 could even be formed of metal, if shaped and given a smooth outer surface which would not cause the user discomfort. An added possibility is that the spacing tips 12 might be fabricated in the form of fluid-filled flexible membranes, as indicated in FIG. 5, for example, for more readily conforming to the interior surfaces of a user's nostrils.

The present invention provides for the repeated accurate and proper placement of the spacing tips 12 through their arrangement at each end of a frame 20. The frame 20 is formed of a material having some spring properties yet retaining a degree of malleability and is configured to resemble a series of compound curves, as seen in elevated side view FIG. 3, top view FIG. 4, and front view FIG. 5.

Figure 3:
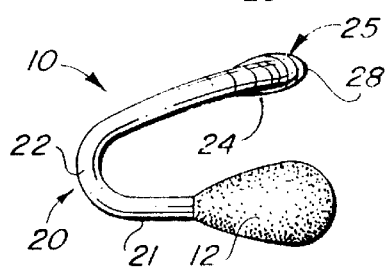
FIG. 3 is an elevated side view of the arrangement of FIG. 1.
Figure 4:
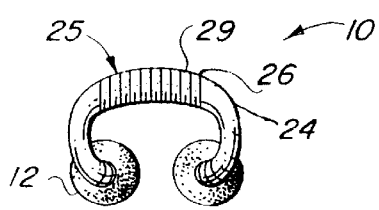
FIG. 4 is an end view of the arrangement of FIG. 1, looking from the right side of the figure.

FIG. 3 shows the spacing tips 12 covering the free ends of a pair of intra-nasal struts 21. The intra-nasal struts 21 are formed adjacent a pair of nasal curves 22. The opposing ends of the nasal curves 22 are formed adjacent the ends of a pair of extra-nasal struts 23. The opposing ends of the extra-nasal struts 23 connect to a pair of saddle curves 24. A saddle 25 extends between, and connects, the saddle curves 24. For additional user comfort, the saddle 25 may be outfitted with a saddle pad 26, positioned over the saddle 25, to cushion the bridge of the user's nose from contact with the saddle 25. The saddle 25 may be provided with an adhesive surface 28, if desired, in order to assist in providing secure positioning of the nasal appliance in place for use. The adhesive surface 28 may be formed integrally with the saddle 25 or, alternatively, it may be disposed upon the saddle after forming thereof. In still another version, the adhesive surface 28 may be applied to the frame by the user. In another version, an adhesive surface 29 may be affixed to the saddle pad 26, rather than to the saddle 25.

Figure 2:
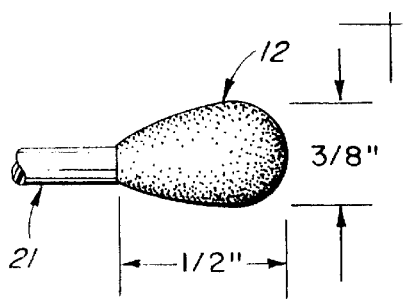
FIG. 2 is a detailed schematic view of one of the spacing tips of the arrangement of FIG. 1, again identifying some of the approximate dimensions of the device.

In one particular preferred embodiment, as indicated in FIGS. 1, 2 and 3, the spacing tips 12 have an outer diameter of ⅜" and a length of ½". The transverse dimension (width) of the saddle 25 is approximately ½" with the spacing between the nasal curves 22 being approximately ⅜". The overall dimension of the frame from the saddle pad 26 to the nasal curves 22 is approximately ¾" whereas the overall dimension from a nasal curve 22 to the end of an associated spacing tip is approximately 1". The distance between spacing tips is approximately ¼". These dimensions may vary proportionally for the variety of sizes of the device 10 provided to accommodate different users.

In use of the device 10, the spacing tips 12 and intra-nasal struts 21 are carefully inserted into the user's nasal fossae (nostrils). The device is gently elevated into the nasal fossae until resistance is felt. The user would then depress the saddle pad 26 onto the nasal dorsum while stabilizing the intra-nasal struts 21 with his thumbs. Customizing the fit of the device may be realized by slightly bending the malleable frame 20, specifically at the nasal curves 22 and the saddle curves 24. When used in this fashion, after perhaps a slight initial adjustment, the device provides increased ease of breathing and relief from snoring without any discomfort. Additionally, the user will be able to achieve the same successful results time and again, due to the capability of the device to be cleaned by washing with soap and water, after which it is ready for re-use.

Figure 7:
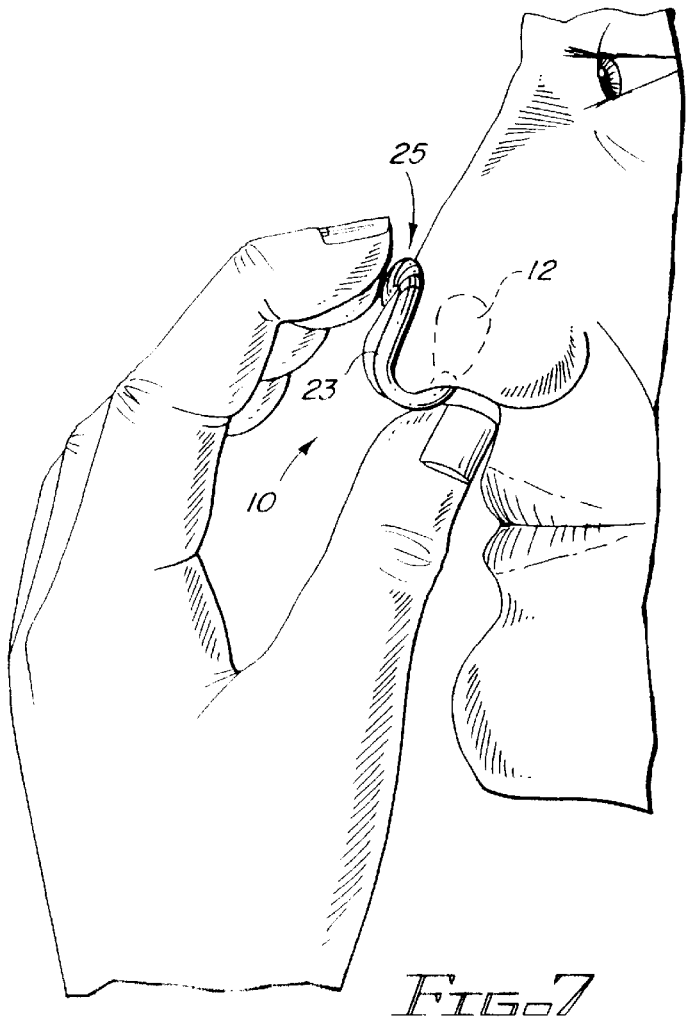
FIG. 7 is a side view showing the device as it would be inserted by a user.

Side view FIG. 7 shows the device 10 being inserted, adjusted and worn by the user. Device 10 is available in a variety of sizes (e.g. small, medium, large) to accommodate all users.

Although there have been described hereinabove various specific arrangements of a nasal appliance in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A nasal appliance for improving nasal breathing and alleviating snoring by reducing breathing resistance and precluding the collapse of the nasal passageway induced by the venturi effect, said nasal appliance comprising:
   a pair of spacing tips for insertion into the nasal fossae to prevent collapse of the cartilages of the nose on inspiration without applying stress to nasal tissue; and
   a frame affixed to said pair of spacing tips to maintain accurate positioning of said spacing tips inside the nasal passageways.

2. The nasal appliance of claim 1, wherein said frame comprises a pair of intra-nasal struts having upper and lower ends, said spacing tips being affixed at the upper ends of said intra-nasal struts, said frame also having an extra-nasal support member attached to the lower ends of said intra-nasal struts.

3. The nasal appliance of claim 2, wherein said extra-nasal support member comprises a pair of nostril curve sections having proximal and distal ends, the distal ends of said nostril curve sections formed adjacent the lower ends of said intra-nasal struts.

4. The nasal appliance of claim 3, wherein said extra-nasal support member further comprises a pair of extra-nasal struts having upper and lower ends, the lower ends of said extra-nasal struts being affixed, respectively, to the proximal ends of said nostril curve sections.

5. The nasal appliance of claim 4, wherein said extra-nasal support member further comprises a saddle member connecting the upper ends of said extra-nasal struts.

6. The nasal appliance of claim 5, wherein said saddle member includes a pad for increasing the comfort of use and reducing irritation to the skin.

7. The nasal appliance of claim 6, wherein said saddle member includes an adhesive surface disposed upon said saddle member for assisting in providing secure positioning of the nasal appliance.

8. The nasal appliance of claim 7, wherein said adhesive surface is integral with said saddle member.

9. The nasal appliance of claim 7, wherein said adhesive surface may be applied to said frame by the user as required.

10. The nasal appliance of claim 7, wherein said adhesive surface is affixed to said pad.

11. The nasal appliance of claim 1, wherein said frame is comprised of plastic.

12. The nasal appliance of claim 1, wherein said frame is comprised of formed metal.

13. The nasal appliance of claim 1, wherein said frame is comprised of bent wire.

14. The nasal appliance of claim 1, wherein said frame is comprised of hard rubber.

15. The nasal appliance of claim 1, wherein said frame is malleable through manual manipulation by the user to facilitate fit and comfort.

16. The nasal appliance of claim 1, wherein said spacing tips are comprised of silicone.

17. The nasal appliance of claim 1, wherein said spacing tips are comprised of plastic.

18. The nasal appliance of claim 1, wherein said spacing tips are comprised of latex rubber.

19. The nasal appliance of claim 1, wherein said spacing tips are comprised of polyurethane.

20. The nasal appliance of claim 1, wherein said spacing tips are comprised of metal.

21. The nasal appliance of claim 1, wherein said spacing tips are comprised of fluid filled flexible membranes.

22. The nasal appliance of claim 1, wherein said spacing tips and frame are integrally formed as a single unit.

23. The nasal appliance of claim 1, wherein each spacing tip has a diameter within the range of $1/16"$ to $3/8"$ and a length within the range of $1/16"$ to $1/2"$, corresponding to variations in size and spacing of the nasal passages of the intended user.

24. The nasal appliance of claim 23, wherein each spacing tip has a diameter of approximately $3/8"$ and a length of approximately $1/2"$.

25. The nasal appliance of claim 5, wherein each spacing tip has a diameter within the range of $1/16"$ to $3/8"$ and a length within the range of $1/16"$ to $1/2"$, corresponding to variations in size and spacing of the nasal passages of the intended user.

26. The nasal appliance of claim 25, wherein each spacing tip has a diameter of approximately $3/8"$ and a length of approximately $1/2"$; and wherein the width of the saddle is approximately $1/2"$, the spacing between the nasal curves is approximately $3/8"$, the overall dimension of the frame from saddle pad to nasal curves is approximately $3/4"$, the distance from a nasal curve to the end of an associated spacing tip is approximately $1"$, and the distance between the spacing tips is approximately $1/4"$.

27. A nasal appliance for improving nasal breathing and alleviating snoring by reducing breathing resistance and precluding the collapse of the nasal passageway induced by the venturi effect, said nasal appliance comprising:
   a frame fabricated of a spring material formed generally in the shape of a pair of Us joined by a transverse bridge and having opposite terminal ends with spacing and dimensions adapted to fit within the nasal passages of an intended user; and
   a pair of spacing tips for insertion into the nasal fossae to prevent collapse of the cartilages of the nose on inspiration without applying stress to nasal tissue, said spacing tips being affixed to respective terminal ends of said frame.

* * * * *